United States Patent [19]

Lövgren et al.

[11] Patent Number: 4,501,813

[45] Date of Patent: Feb. 26, 1985

[54] BIOLUMINESCENCE METHOD FOR DETERMINING NADH OR NADPH

[75] Inventors: Timo Lövgren, Vallaojantie; Jukka Lavi, Karjatie, both of Finland

[73] Assignee: Wallac OY, Turku, Finland

[21] Appl. No.: 390,710

[22] Filed: Jun. 21, 1982

[30] Foreign Application Priority Data

Jun. 25, 1981 [SE] Sweden .................................. 8103980

[51] Int. Cl.$^3$ .......................... C12Q 1/66; C12Q 1/26; C12N 9/96
[52] U.S. Cl. ......................................... 435/8; 435/25; 435/188
[58] Field of Search ..................... 435/8, 25, 188, 190, 435/810

[56] References Cited

U.S. PATENT DOCUMENTS

| | | | |
|---|---|---|---|
| 4,234,681 | 11/1980 | DeLuca-McElroy | 435/8 |
| 4,278,760 | 7/1981 | Wulff et al. | 435/26 |
| 4,278,761 | 7/1981 | Hastings et al. | 435/8 |

OTHER PUBLICATIONS

Hastings, J. W., "Methods in Enzymology, Bioluminescence and Chemiluminescence" (1978), (S. Colowick and N. Kaplan ed., vol. 57, 125–236 Academic Press, N.Y.
Hastings, J., and Nealson K., Annual Review of Microbiology, (1977), 31, 549–595.
Brolin, S., Bioelectrochem. Bioenerg., (1976), 4, 257–262.
Golden, S., and Katz, J., Biochem. J. (1980), 188, 799–805.
Jablonski, E., and DuLuca, M., Clin. Chem., (1979), 25, 1622–1627.
Ford, J., and DeLuca, M., Anal. Biochem., (1981), 110, 43–48.
Thore, A., Ann. Clin. Biochem., (1979), 16, 359–369.
Duane, W., and Hastings, Jr., Molec. Cell. Biochem., (1975), 6, 53–64.
Tu, S.C., and Hastings, J., Proc. Natl. Acad. Sci. USA, (1980), 77, 249–252.
Jablonski, E., and DeLuca, M., Biochemistry, (1977), 16, 2932–2936.
Gerlo, E., and Charlier, J., Eur. J. Biochem., (1975), 57, 461–467.
Hastings, J., Spudich, J., and Malnic, G., J. Biol. Chem., (1963), 238, 3100–3105.
Hastings, J., Riley, W., and Marsa, J., J. Biol. Chem., (1965), 240, 1473–1480.

*Primary Examiner*—Esther M. Kepplinger
*Attorney, Agent, or Firm*—Fisher, Christen & Sabol

[57] ABSTRACT

A method for determining NADH and/or NADPH-concentrations, for instance in NADH- or NADPH transforming systems, the method comprising the step of bringing the sample subject to determination in contact with the bioluminescent reagent based on bacteria luciferase, NAD(P)H-FMN oxidoreductase, FMN and aliphatic aldehyde, whereby a reaction takes place, where NAD(P)H is oxidized and FMN is reduced, the reaction being catalyzed by the oxidoreductase, whereafter the $FMNH_2$ formed and the aldehyde are bound to the luciferase and light is emitted, the intensity of this light being measured and constituting a measure of the NADH- or NADPH-concentration, whereby in the determination a bacteria luciferase purified so as not to obtain any oxidoreductase is used in combination with a predetermined amount of oxidoreductase, this amount being such that a stable light intensity is obtained in the presence of a constant amount of NADH or NADPH whereby an internal calibration can be carried out in NADH or NADPH transforming systems by adding a predetermined amount of NADH or NADPH followed by a subsequent measuring of the increase of the light intensity.

5 Claims, 5 Drawing Figures

BIOLUMINESCENCE METHOD FOR DETERMINING NADH OR NADPH

BACKGROUND OF THE INVENTION

The present invention refers to a method for determining NADH and/or NADPH-concentrations, for instance in NADH- or NADPH transforming systems, the method comprising the step of bringing the sample subject to determination in contact with the bioluminescent reagent based on bacteria luciferase, NAD(P)H-FMN oxidoreductase, FMN and aliphatic aldehyde, whereby a reaction takes place, where NAD(P)H is oxidized and FMN is reduced, the reaction being catalyzed by the oxidoreductase, whereafter the $FMNH_2$ formed and the aldehyde are bound to the luciferase and light is emitted, the intensity of this light being measured and constituting a measure of the NADH- or NADPH-concentration.

PRIOR ART

NADH is the commonly used abbreviation for reduced nicotine-amide adenine dinucleotide and NADPH is the corresponding abbreviation for reduced nicotine amide adenine dinucleotide phosphate. Bacteria bioluminescent reagents related to the concentrations of these compounds are known per se, these reagents being based on the enzymes luciferase and NAD(P)H-FMN oxidoreductase and flavine mononucleotide (FMN) and aliphatic long chained ($C_8$-$C_{14}$) aldehyde to which NAD(P)H has to be added in order to obtain a light emission. When NAD(P)H is brought into contact with the reagent, a reaction or rather a sequence of enzyme catalyzed reactions takes place. The reactions have been studied in detail for enzymes from several different luminescent bacteria, and these reactions represent the basis of the technique. Several surveys have been published recently; (Hastings, J. W. (1978), "Methods in Enzymology, Bioluminescence and Chemiluminescence", (S. Colowick and N. Kaplan ed., Vol. 57, 125-236, Academic Press, New York and Hastings, J. and Nealson, K. (1977), Annual Review of Microbiology, 31, 549-595).

The determination of NAD(P)H has usually been carried out in such a way that the sample having an unknown concentration of NAD(P)H has been mixed with the bioluminescence reagent containing luciferase, NAD(P)H-FMN oxidoreductase, FMN and aliphatic aldehyde. Often unpure luciferase preparations have been used which contain both luciferase and oxidoreductase whereby no addition of oxidoreductase has been made (see for instance Brolin, S. (1976), Bioelectrochem. Bioenerg. 4, 257-262 and Golden, S. and Katz, J. (1980), Biochem. J. 188, 799-805). Purified enzymes have however become used (see Jablonski, E. and DeLuca, M. (1979) Clin. Chem. 25, 1622-1627, and Ford, J. and DeLuca, M. (1981) Anal. Biochem. 110, 43-48). The addition of NAD(P)H to the bioluminescent reagent gives rise to a light emission the intensity of which decreases relatively fast, since NAD(P)H is consumed and a constant reaction rate cannot be reached (see Thore, A. (1979) Ann. Clin. Biochem. 16, 359-369). The concentration of NAD(P)H has thus been determined either by measuring the initial speed of the reaction, the maximum reaction speed or by means of integration of the reaction speed (light intensity) during a predetermined time which has made it difficult to reach reproducible results.

The investigation of bacteria bioluminescence systems has however given the information that the light kinetics obtained when measuring NAD(P)H rates mainly varies in dependence of the purity and activity of the enzyme preparation (see Duane, W. and Hastings, J. (1975), Molec. Cell. Biochem. 6, 53-64, Jablonski, E. and DeLuca, M. (1979), Clin. Chem. 25, 1622-1627 and Tu, S-H. and Hastings, J. (1980) Proc. Natl. Acad. Sci. U.S.A. 77, 249-252). The difficulties in preparing reagents in a reproducible way have however implied that the bacteria luciferase system has not been widely used, although some commercial reagents are available in the market.

BROAD DESCRIPTION OF THE INVENTION

According to the invention additions to an NAD(P)H dependent bioluminescence reagent result in a light emission which during the complete measuring time is proportional to the NAD(P)H concentration. As the bioluminescent reagent consumes negligible amounts of NAD(P)H samples, the NAD(P)H concentration of each is constant, thereby generating a stable and constant light emission which facilitates the use of the reagent for NAD(P)H determination. The properties of the reagent makes it possible to carry out an internal calibration of the system by adding a known amount of NAD(P)H whereafter the increase in light intensity is used for calculating the final result of the analysis. Furthermore, reagents with properties as specified above could be added to other NAD(P)H transforming systems in order to monitor in a simple way the change of NAD(P)H concentration by means of a continuous measuring of the light intensity. NAD(P)H transforming systems could for instance be combinations of enzymes or possibly substrates which in their transformation gives rise to forming or consuming of NAD(P)H. An internal calibration of a known concentration of NAD(P)H could also be carried out in these applications. The analytic use of the reagent comprises the determination of NAD(P)H and substances and enzymes taking part in NAD(P)H-transforming reactions within clinical chemistry and clinical microbiology as well as in biochemical and biological research.

DETAILED DESCRIPTION OF THE INVENTION

The invention will now be described in detail, reference being made to the enclosed drawing in which:

FIG. 1 schematically shows a sequence of enzyme catalyzing reactions obtained when NAD(P)H is brought in contact with a bacterial luminescent reagent;

Figure 1:
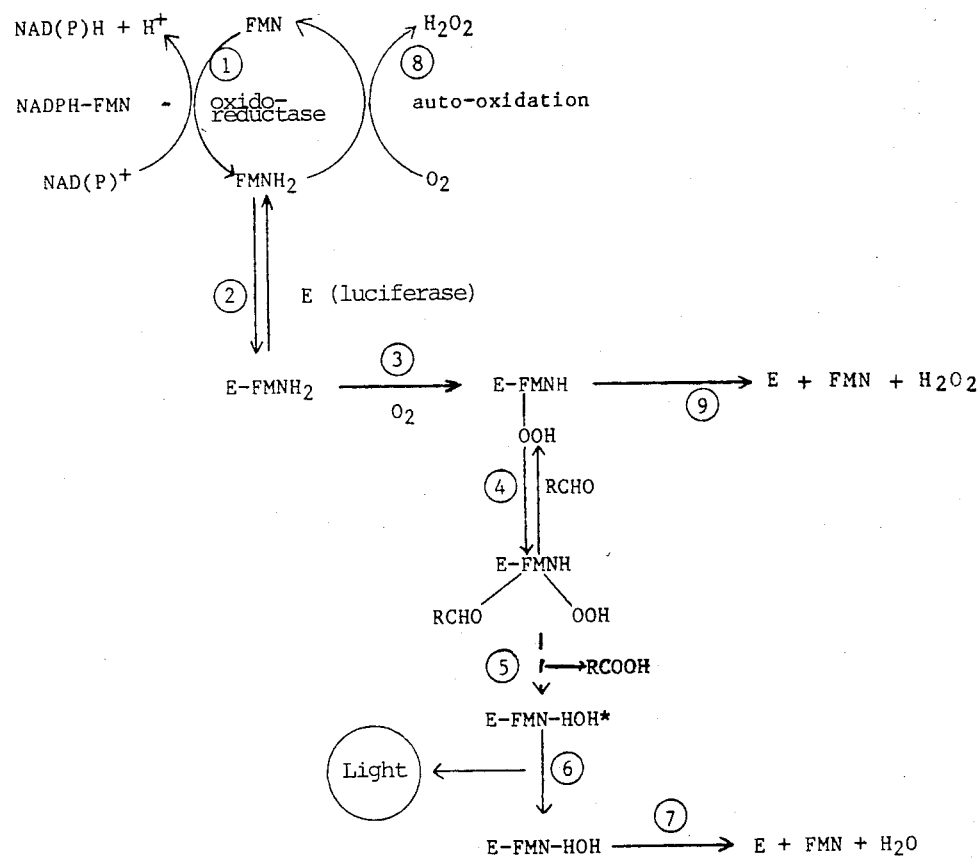

In reaction 1 in FIG. 1 reduced pyridine coenzyme (NADH or NADPH) reacts with FMN whereby the reaction is catalyzed by a specific NAD(P)H-FMN oxidoreductase whereby as end products are formed reduced flavine coenzyme FMNH$_2$ and oxidized pyridine coenzyme (NAD or NADP). Oxidoreductases which are specific for the two possible pyridine coenzymes, have been found in and isolated from the luminescent bacteria *Beneckea harveyi* (see Jablonski, E. and DeLuca, M. (1977), Biochemistry, 16, 2932–2936 and Gerlo, E. and Charlier, J. (1975), Eur. J. Biochem, 57, 461–467).

In reaction 2 FMNH$_2$ is rapidly and solidly bound by luciferase.

In reaction 3 the enzyme FMNH$_2$ complex reacts with O$_2$ in order to form an oxigenerated form of reduced flavine and remains bound to the enzyme. This oxigenerated intermediate product has a long life time and it has even been isolated at low temperatures.

In reaction 4 the long chained aliphatic aldehyde is bound to the enzyme and is oxidated by peroxide intermediate products to the corresponding fatty acid which is released (reaction 5). Aldehydes with carbon-hydrogen chains of various length have been used (see Hastings, J., Spudich, J. and Malnic, G. (1963), J. Biol. Chem. 238, 3100–3105). When the fatty acid is released in reaction 5, hydroxylated FMNH is formed which is enzyme bound and is considered to be the electronically excited molecule.

In reaction 6 the excited state is transformed to the original state while emitting a photon. In the last stage (reaction 5) the end products are dissociated from the enzyme which could then take form in a new catalytic cycle.

Reactions 7 and 8 constitute side reactions of the bacteria luciferase system. From these, especially reaction 8, the fast autooxidation of FMNH$_2$ disturbs the determination of NAD(P)H as it oxidates the FMNH$_2$ formed. The enzymatic side reaction (reaction 7) will not disturb the determination in presence of aliphatic aldehyde. The presence of side reactions, the lack of pure enzyme and uncontrolled reaction conditions have been the most important reasons for giving rise to a light flash with a varying half life instead of a constant light emission when determining NAD(P)H in a bacteria luciferase system.

According to the present invention it has been shown that it is possible to control the light kinetics of the luciferase system by using purified luciferase and NAD(P)H-FMN oxidoreductase in varying rates. It has previously been shown that the light intensity (the reaction rate) by using luciferase and oxido-reductase is proportional to the product of the concentrations o the enzymes present (see Hastings, J., Riley, W. and Marsa, J. (1965), J. Biol. Chem. 240, 1473–1480), but furthermore the light kinetics is affected. By carefully controlling the amounts of enzyme added, especially the oxidoreductase concentration, it has become possible to prepare a reagent with the desired properties, i.e. a bacteria luciferase reagent containing luciferase NAD(P)H-FMN oxidoreductase, FMN and aliphatic aldehyde with a stable light level.

Figure 2:
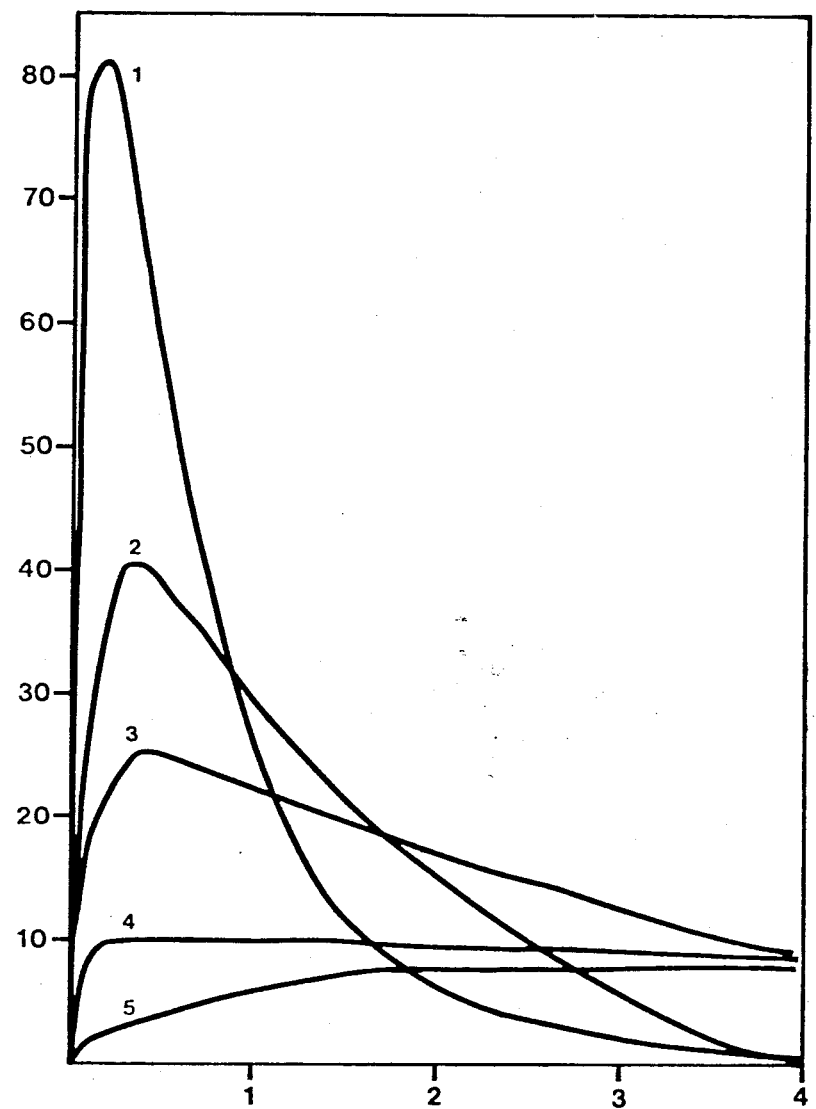
FIG. 2 shows the effect of the oxidoreductase reaction on the light kinetics of the bacteria luciferase reaction.

This is illustrated from FIG. 2 which shows a characteristic experiment where the bacteria luciferase system has been used for the determination of NADH. Along the abscissa time is indicated in minutes and along the ordinate the light intensity in mV for a number of experiments (1–5) which have been carried out in 0.1M phosphate buffer pH 7 containing 0.5 mM DTT, 0.1% BSA, $2 \times 10^6$M FMN and $2 \times 10^5$ dekanal. The reactions were initiated by adding $5 \times 10^{-12}$M NADH to 0.5 ml reaction mixture. The enzyme concentrations in the experiments were as follows:

| Experiment No. | Oxidoreductase U/l | Luciferase kV/l |
| --- | --- | --- |
| 1 | 25 | 45 |
| 2 | 16 | 40 |
| 3 | 11 | 40 |
| 4 | 3 | 45 |
| 5 | 0.6 | 110 |

The luciferase concentration in experiment 5 was higher only to obtain sufficient light intensity. As appears from the figure a high oxidoreductase rate in the system gives a relatively fast decreasing light kinetics. If a lower amount of oxidoreductase is used, the light intensity decreases slower until the rate reaches a level (experiment 4) which gives a substantially stable light intensity. A further reduction of the amounts of oxidoreductase gives a reagent mixture where the light intensity increases slower and slower until a constant level is finally reached. The fact that the light intensity is different in the five experiments depends on the fact that it is proportional to the product of the concentrations of the enzymes present. The amount of luciferase used affects the light intensity but does not have any significant affect on the light kinetics, whereas the oxidoreductase amount affects both the light intensity and the light kinetics. The decreasing light intensity is explained by the fact that the oxidoreductase consumes the NADH which exists in the system whereby an equivalent amount of FMNH$_2$ is formed which partly takes part in the luciferase reaction and is then partly autooxidated. When the oxidoreductase concentration is decreased and a stable light level is reached, the enzyme present has an activity level which achieves a continuous constant oxidation of NADH and a corresponding constant reduction of an equivalent amount of FMN. The end result is a reaction system where the amount of NADH present in the sample determines the intensity of the stable light. The corresponding reaction system can be designed for determining of NADPH.

The bacteria luciferase system is subject to the Michealis-Menten kinetics. At a low substrate concentration the light intensity is proportional to the amount of NAD(P)H provided that the concentration is well below K$_m$ for the substrate. Relations could be expressed in the following formula:

$$v = I = \frac{V_{max} + S}{K_m + S} S < <K_m \frac{V_{max}}{K_m} \times S$$

The reaction rate (light intensity = I) will furthermore be constant if the transformation is sufficiently slow so that the substrate concentration will not change substantially during the measuring which requirements in principal are met with by the bacteria luciferase reagent developed.

Figure 3:
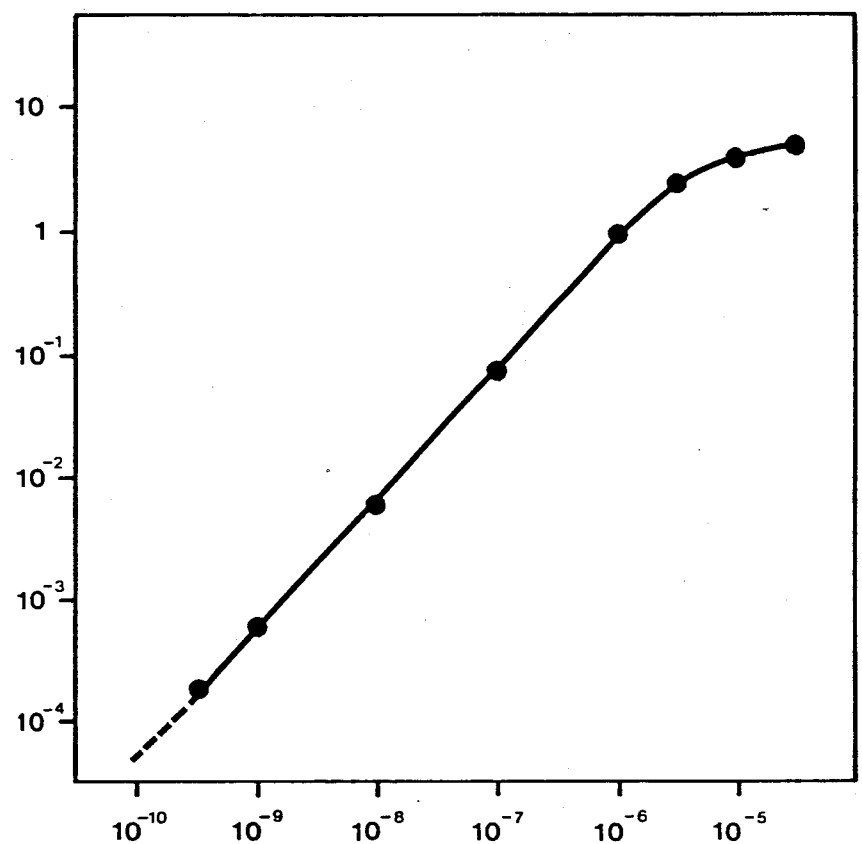
FIG. 3 shows a standard curve for NADH obtained with a bacteria luciferase reagent having a stable light intensity.

In FIG. 3 where along the abscissa the concentration in molar of NADH is indicated and along the ordinate the light intensity in Volt is indicated, there is shown a standard curve for NADH-determination with the bacteria luciferase reagent containing NADH-FMN oxidoreductase. The corresponding standard curve is obtained for NADPH if the reagent contains NADPH-FMN oxidoreductase. The reagent could be used within a very wide concentration range. The sensitivity of the system could furthermore be increased either by decreasing the reaction volume while maintaining the amounts of enzyme constant or by increasing the amount of luciferase in the reagent.

Figure 4:
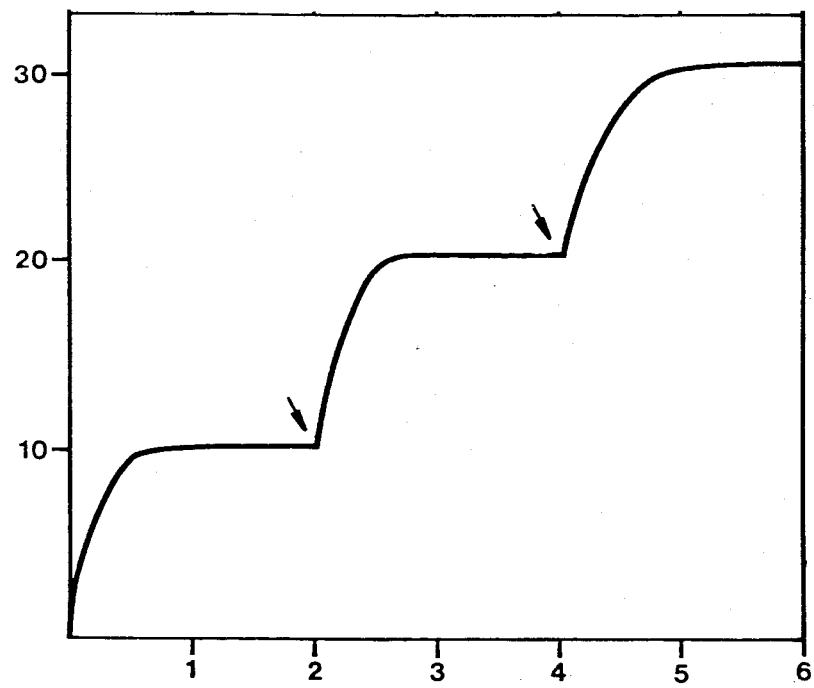
FIG. 4 shows the determination of NADH-concentrations by using internal calibration.

FIG. 4 shows a typical result when determining NADH (or NADPH) rates in a sample. In the experiment $5 \times 10^{-11}$ NADH was added to a reagent containing 0.1M phosphate buffer pH 7.0, 0.5 mM DTT, 0.1% BSA, $2 \times 10^{-6}$M FMN, $2 \times 10^{-5}$M dekanal, 4 U/l oxidoreductase and 110 kV/l luciferase. The arrows indicate the point of time for addition of further $5 \times 10^{-11}$ mol NADH. When a sample is added, the light intensity increases to a constant level and is maintained there for about 10 minutes whereafter it slowly decreases as a function of time (I=5%/min) due to the oxidoreductase consumed in the reagent. The bacteria luciferase reagent developed makes it possible to carry out the analysis by using an internal calibration with a predetermined amount of NADH. The light intensity rises to a new constant level which is dependent upon the amount of NADH added.

Figure 5:
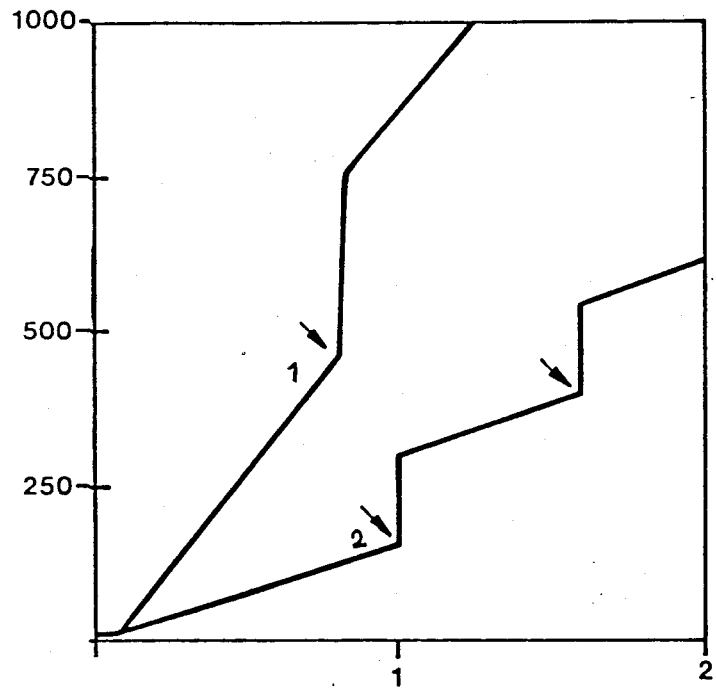
FIG. 5 shows a kinetic determination of alcohol dehydrogenase activity by using internal calibration with a predetermined amount of NADH.

The optimized bacteria luciferase reagent could be used for endpoint analyses of metabolites which are enzymatically transformed to equivalent amount of NADH, for kinetic analysis of the corresponding metabolites and for kinetic determinations of enzyme activities. FIG. 5 shows the result of an experiment where the bacteria luciferase reagent has been used for the determination of alcohol dehydrogenase activity. The experiment conditions were as follows: 0.9 (1) and 0.25 (2) mU alcohol-dehydrogenase was added to 0.5 ml reagent mixture containing 0.1M phosphate buffer pH 7.0, 0.5 mM DTT, 0.1% BSA, $2 \times 10^{-6}$M FMN, $2 \times 10^{-5}$M dekanal, $8 \times 10^{-5}$M NAD, $8 \times 10^{-5}$M ethanol 4 U/l oxidoreductase and 110 kV/l luciferase. The arrows indicates the point of time for the internal calibration with a predetermined amount of NADH, $1.5 \times 10^{-10}$ mol in reaction 1 and $7.5 \times 10^{-11}$ mol in reaction 2. The increase of the light intensity in mV/min is a measure of the enzyme activity which could also be calculated by using the relatively fast increase in mV which is obtained at an internal calibration with a predetermined amount of NADH.

The experiments described (FIGS. 2-5) should be considered as non-limiting examples of applications of the invention.

We claim:

1. Method for determining NADH-concentration and/or NADPH-concentration in sample, comprising contacting the sample with a bioluminescent reagent based on bacterial luciferase, NAD(P)H-FMN oxidoreductase, FMN and aliphatic aldehyde, whereby a reaction takes place, where NAD(P)H is oxidized and FMN is reduced, the reaction being catalyzed by the oxidoreductase, whereafter the $FMNH_2$ formed thereby and the aldehyde are bound to the luciferase and light is emitted, the intensity of such light being measured and constituting a measure of the NADH-concentration or NADPH-concentration, characterized in that the bacterial luciferase is used in combination with an amount of oxidoreductase which consumes a negligible amount of NADH or NADPH in the sample so that a constant light intensity is obtained in the presence of a constant amount of NADH or NADPH, the amount of NAD(P)H-FMN oxidoreductase per analysis being 0.2 to 20 mU, wherein U is the amount of enzyme catalyzing the oxidation of 1 μmol of NADH or NADPH per minute, and the amount of bacterial luciferase per analysis being 0.8 to 80 ug.

2. Method as claimed in claim 1 wherein the aliphatic aldehyde has a carbon hydrogen chain of 8 to 14 carbon atoms.

3. Method as claimed in claim 1 wherein the amount of aldehyde per analysis is $2 \times 10^{-7}$ to $2 \times 10^{-9}$ mol.

4. Method as claimed in claim 3 wherein the amount of FMN per analysis is $2 \times 10^{-8}$ to $2 \times 10^{-10}$ mol.

5. Method as claimed in claim 1 wherein an internal calibration is carried out by adding a predetermined amount of NADH or NADPH followed by a subsequent measuring of the increase of the light intensity.

* * * * *